United States Patent [19]

Feeny

[11] 4,170,464
[45] Oct. 9, 1979

[54] HERBICIDAL COMBINATIONS

[75] Inventor: Richard W. Feeny, Hightstown, N.J.

[73] Assignee: American Cyanamid Company, Stamford, Conn.

[21] Appl. No.: 822,504

[22] Filed: Aug. 8, 1977

Related U.S. Application Data

[60] Continuation-in-part of Ser. No. 518,020, Oct. 25, 1974, abandoned, which is a division of Ser. No. 307,670, Nov. 17, 1972, Pat. No. 3,867,403.

[51] Int. Cl.$^2$ .............................................. A01N 9/22
[52] U.S. Cl. ........................................ 71/92; 71/108; 71/109; 71/110; 71/116; 71/117
[58] Field of Search ............................ 71/92, 116, 117

[56] References Cited

U.S. PATENT DOCUMENTS

| | | | |
|---|---|---|---|
| 2,972,528 | 2/1961 | Brian et al. | 71/116 |
| 2,992,913 | 7/1961 | Pfeiffer | 71/116 |
| 3,151,970 | 10/1964 | Lush et al. | 71/116 |
| 3,288,586 | 11/1966 | Littler | 71/116 |
| 3,922,161 | 11/1975 | Walworth et al. | 71/92 |

OTHER PUBLICATIONS

Berezovskii et al., "The Combination of 2,4-D with, etc.;" (1965), CA 65, p. 7921 (1966).

*Primary Examiner*—Glennon H. Hollrah
*Attorney, Agent, or Firm*—H. G. Jackson

[57] ABSTRACT

This invention is (1) synergistic combinations of a 1,2-dialkyl-3,5-diphenylpyrazolium salt and a 2,4-dichlorophenoxy acetic acid or the salts and esters thereof, or 4-chloro-2-methylphenoxy acetic acid or the salts or esters thereof useful as herbicides; (2) a salt of a 1,2-dialkyl-3,5-diphenylpyrazolium cation and certain halophenoxy acetate anions useful as herbicides and (3) the synergistic combination of 1, above, with the salt of 2, above, present.

11 Claims, No Drawings

HERBICIDAL COMBINATIONS

CROSS REFERENCE TO RELATED APPLICATIONS

This application is a continuation-in-part application of co-pending Ser. No. 518,020 now abandoned filed Oct. 25, 1974 which is a division of Ser. No. 307,670 filed Nov. 17, 1972 and is now U.S. Pat. No. 3,867,403 (1975). Herbicidal activity of some of the 1,2-dialkyl-3,5-diphenylpyrazolium salts useful in the combinations of the invention is reported in Klingsberg and Walworth U.S. Pat. No. 3,882,142 (1975).

BACKGROUND OF THE INVENTION

1. Field of the Invention

The invention pertains to chemicals for herbicidal use.

2. Description of the Prior Art

Although 2,4-dichlorophenoxy acetic acid (2,4-D) and 4-chloro-2-methylphenoxy acetic acid (MCPA) and the esters and salts of these compounds are well known, commercially available, herbicides widely used for control of broadleaf weeds, such compounds ahve demonstrated no discernible herbicidal effect on wild oats (Avena spp.) at rates of application normally used for broadleaf weed control in the presence of economic crops. By itself, this observation would not be considered particularly important, since one would normally expect that a compound could be found which would provide adequate wild oat control, and that a mixture of said wild oat herbicide and the phenoxyacetic acid, ester or salt, would then provide effective control for both wild oats and broadleaf weeds. Unfortunately, however, the problem is not quite so simple.

Wild oats (Avena spp.) are of the family Graminae, the same family in which the small grains, such as wheat and barley are classified. They react to most chemicals in the same manner as the other members of the family, and thus are particularly difficult to control in the presence of economically important grain crops in said family. It is not, therefore, surprising that a considerable effort was required to find several chemicals which provide the selectivity required to achieve wild oat control in the presence of the grains mentioned. The most widely accepted of these are 4-chloro-2-butynyl N-(3-chlorophenyl)carbamate (BARBAN) and the ethyl ester of N-benzoyl-N-(3,4-dichlorophenyl)alanine (SD-30053). They are very effective wild oat control agents when used alone, but unfortunately, when they are combined with the most widely accepted of the systemic or hormonal broadleaf herbicides utilized in the cultivation of small grains, i.e. 2,4-D, MCPA and the esters and salts thereof, the compounds are antagonistic and wild oat control is lost.

These findings are well documented in the literature in articles, such as have appeared in Weeds Today, pg. 13, July of 1970, or in the following articles: "Studies of Barban Selectivity for Wild Oat in Wheat," R. W. Neidermyer, Fargo, North Dakota, Dissertation Abstr. Intern. 31, No. 11, 6383-B-84-B, 1971; "Antagonistic Effect of 2,4-D Amine and SD-30053 on Wild Oats," D. R. Colbert and A. P. Appleby, Corvallis, Oregon, Res. Prog. Rept. West. Soc. Weed Sci., March, 1972, 118–119; "SD-30053 Plus Broadleaf Herbicides," John D. Nalewaja, The Research Report of North Central Weed Control Conference, 1971, pgs. 32-33; "In General, Members of the Grass Family are Resistant to 2,4-D While Most Broadleaf Plants are Susceptible," Weed Control, Robbins, Crafts and Razner, page 9, McGraw Hill, 2nd Edition, 1952; and "Wild Oats are Resistant to 2,4-D," Weed Control as a Science, Klingman, page 388, Wiley, 1961.

In the light of the fact that few compounds have been found which provide selective control of wild oats in the presence of grass grain crops, and further that the most widely accepted of those which are selective are inactivated when combined with the broadleaf control agents, 2,4-D an MCPA, it is surprising to find a compound (i.e. a 1,2-dialkyl-3,5-diphenylpyrazolium salt) that is selective for control of wild oats and also exhibits enhanced wild oat activity when used in combination with systemic or hormonal broadleaf herbicides, i.e. 2,4-D, MCPA or the esters, salts or mixtures thereof.

SUMMARY OF THE INVENTION

The invention is synergistic herbicidal combinations comprising (a) a 1,2-dialkyl-3,5-diphenylpyrazolium salt of the formula:

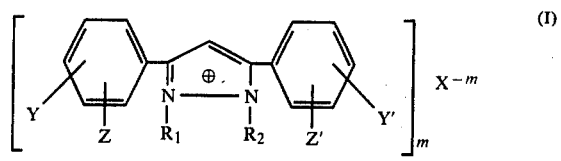

wherein $R_1$ is methyl; $R_2$ is alkyl $C_1$–$C_4$; X is an anion with a charge of 1 to 3; Y, Y', Z and Z' are hydrogen, halogen, methyl or methoxy; and m is an integer of 1, 2 or 3; provided that only one phenyl ring can be substituted on the carbon para to the pyrazolium ring with a substituent other than hydrogen; and (b) a phenoxyacetic acid, ester or salt of the formula

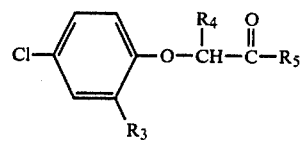

wherein $R_3$ is Cl or methyl; $R_4$ is hydrogen or methyl; $R_5$ is $-OR_6$ or $-OM$; $R_6$ is hydrogen, alkyl $C_1$–$C_8$ (preferably methyl, ethyl, isopropyl, butyl, pentyl, ethylhexyl, octyl or isooctyl), alkoxyalkyl $C_2$–$C_8$ (preferably butoxyethyl or 2-butoxyethyl) and tetrahydrofurfuryl; and M is a alkali metal ion (preferably $Na^\ominus$ or $K^\ominus$),

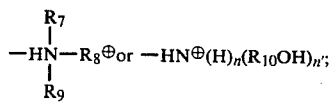

$R_7$, $R_8$ and $R_9$ are hydrogen or alkyl $C_1$–$C_4$; $R_{10}$ is alkylene $C_1$–$C_4$; n is an integer of 0, 1 or 2; n' is an integer of 1, 2 or 3; and the sum of n and n' is 3, or mixtures of the acid, ester or salt.

The invention includes salts of the pyrazolium cation and certain halophenoxyacetate anions of the formula:

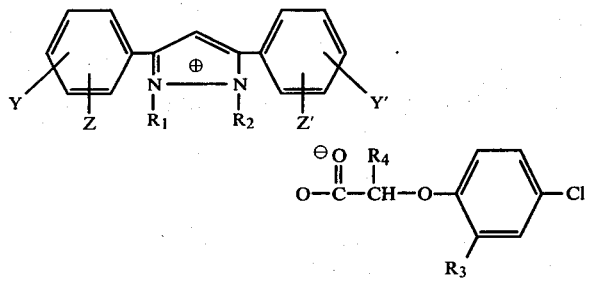

where $R_1$, $R_2$, $R_3$, $R_4$, Y, Y', Z and Z' are as described above. These new compounds are also useful herbicides and may be present in the synergistic herbicidal combination, above.

Suitable halogen substituents for formula (1) compounds include, for example, fluoro, chloro, bromo and iodo. The chloro, fluoro and bromo groups are preferred. Suitable anions include, for example, halides, such as chloride, bromide or iodide; acetate; sulfate, hydroxide; hydrogen sulfate; methyl sulfate; benzene sulfonate; $C_1$-$C_4$ alkoxy benzene sulfonate; $C_1$-$C_3$ alkyl benzene sulfonate, preferably a toluene sulfonate, such as p-toluene sulfonate; nitrate; phosphate; carbonate; hydrogen carbonate; chlorate; thiocyanate; $C_1$-$C_4$ alkane sulfonate; perchlorate; $Br_3^-$, $I_3^-$ and

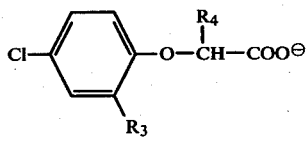

This invention also relates to a method for the postemergence control of wild oats (Avena spp., such as *A. fatua*, *A. sterilis* and *A. ludoviciana*) and undesirable broadleaf plants, and involves the application of a herbicidally effective amount of (1) the synergistic combination, (2) the salt or (3) a composition containing both, to the foliage of said undesirable plant species.

PREFERRED EMBODIMENTS

In accordance with this invention, the synergistic herbicidal combination comprising the 1,2-dialkyl-3,5-diphenylpyrazolium salt and the chlorophenoxyacetic acid, ester or salt or the salts of the pyrazolium cation and the halophenoxyacetate anion, is generally dispersed in water and applied as an aqueous spray to the foliage of the undesirable plants. Water soluble salts of both the pyrazolium and the halophenoxy compounds can be dissolved in the water and applied as such to the foliage of the undesirable plants. Where desired, a surfactant, spreader, sticker, or the like, can also be added to the solution, and addition of a surfactant, such as a linear alkyl polyoxyethylene ether, to the mixture is generally preferred. The pyrazolium salts and the phenoxy compounds may also be individually prepared as wettable powder formulations, emulsifiable concentrates, water miscible concentrates, or the like, and mixed in the spray tank in the field. Any of the commercially available phenoxy acetic acid, esters or salt formulations may, of course, be used. Typical ester formulations which can be used are as follows:

(1) 68% by weight of 2-ethylhexyl ester of 2,4-D, 27% by weight of kerosene and 5% of a blend of oil soluble sulfates with polyoxyethylene ethers;

(2) 40% by weight of butyl 2,4-D, 57% xylene and 3.0% by weight of a blend of oil soluble sulfates with polyoxyethylene ethers;

(3) 45% by weight of isopropyl 2,4-D, 52% heavy aromatic solvent (Panasol AN-3) and 3.0% by weight of a linear alkyl polyoxyethylene ether.

Typical wettable powder formulations of the pyrazolium salt and the halophenoxyacetic acid, ester or salt, contain from about 25% to 57% by weight of the active compound, 20% to 71.5% by weight of a finely divided carrier, such as attapulgite, kaolin, silica, or the like, 1.5% to 3% by weight of a surfactant, such as sodium N-methyl-N-oleoyl taurate ester of sodium isothionate, alkyl phenoxy polyoxyethylene ethanol, or the like, and 2% to 3% by weight of a dispersant, such as a highly purified sodium lignosulfonate, naphthalene sulfonic acid condensate, or the like.

For effective control of undesirable plants, the synergistic herbicidal combination is normally applied in sufficient amount to provide from about 0.25 pound to 2.0 pounds per acre, and preferably 0.50 pound to 1.0 pound per acre, of the pyrazolium cation, and from about 0.13 pound to 1.0 pound per acre, and preferably 0.25 pound to 0.50 pound per acre, of the phenoxyacetic acid equivalent as the acid, ester or salt.

While the synergistic herbicidal combinations of this invention have been indicated to be useful for controlling wild oats and broadleaf weeds in the presence of the agronomically important crops, wheat and barley, the combinations are also found to be useful for the control of these undesirable plant species in the presence of other crops, such as rye, flax and peas.

The invention is further demonstrated by the examples below, which are presented as illustrative and are not to be considered as limitative.

The postemergence herbicidal activity of the synergistic combinations of the invention is demonstrated by the data reported in Tables I, II and III, below.

EXAMPLE 1

In the tests of Table I, wild oats (*Avena fatua*) are grown in flats in the greenhouse until they reach the four-leaf stage. They are then sprayed with an aqueous solution containing a sufficient amount of test compound to provide from about 0.15 pound per acre to 0.60 pound per acre of pyrazolium cation. For comparison, test compounds are used alone and in combination with 4-chloro-2-methylphenoxyacetic acid (MCPA), added in sufficient amount to provide 0.25 pound per acre of said compound.

All test solutions are prepared in such a manner as to contain about 0.1% by weight of the biodegradable nonionic linear alkyl polyoxyethylene ether marketed by Union Carbide Corporation as "Surfel 4884." Untreated plants are used as controls, and four weeks after treatment the foliage of all plants is harvested and weighed.

Data obtained are reported in Table I below, where it can be seen that the addition of 4-chloro-2-methylphenoxyacetic acid to solutions containing a 1,2-dialkyl-3,5-diphenylpyrazolium salt markedly enhanced wild oat control; whereas, addition of 4-chloro-2-methylphenoxyacetic acid to the commercially available wild oat herbicide, 4-chloro-2-butynyl N-(3-chlorophenyl)-carbamate, nullifies wild oat control.

TABLE I

| Treatment | Pound Per Acre | % Inhibition of Wild Oat Foliage weight | |
|---|---|---|---|
| | | No MCPA Added | MCPA added at ¼ lb./Acre** |
| Water | | 0 | 0 |
| 1,2-Dimethyl-3,5-diphenyl-pyrazolium toluenesulfonate | 0.15* | 45 | 62 |
| 1,2-Dimethyl-3,5-diphenyl-pyrazolium toluenesulfonate | 0.30* | 53 | 73 |
| 1,2-Dimethyl-3,5-diphenyl-pyrazolium chloride | 0.60* | 53 | 69 |
| 4-Chloro-2-butynyl N-(3-chlorophenyl)carbamate | 0.50 | 59 | 0 |

*Rate given in pounds per acre for pyrazolium cation.
**Rate given in pounds per acre of acid equivalents applied as the dimethylamine salt.

EXAMPLE 2

Wild Oat Control in the Presence of Hard Red Spring Wheat

In these tests, wild oats (Avena sp.) at the four-leaf stage, growing in the presence of hard red spring wheat, is sprayed with an aqueous solution of the test compound, 1,2-dimethyl-3,5-diphenylpyrazolium methylsulfate, in sufficient amount to provide 0.5 pound per acre of active cation or with an aqueous solution containing 0.5 pound per acre of the active cation plus 0.375 pound per acre of 4-chloro-2-methylphenoxy acetic acid.

Each solution also contains 0.5% by weight of the surfactant "Surfel 4884," a linear alkyl polyoxyethylene ether, marketed by Union Carbide Corporation. Six weeks after treatment, the fields are examined and the percent control of wild oats is determined. Four replicates per treatment are used and reported in Table 2 below.

TABLE 2

| Treatment | Pound Per Acre* | % Control of Wild Oats Replicates | | | | |
|---|---|---|---|---|---|---|
| | | I | II | III | IV | Ave. |
| 1,2-Dimethyl-3,5-diphenyl-pyrazolium methyl sulfate | 0.50 | 40 | 40 | 50 | 50 | 45 |
| 1,2-Dimethyl-3,5-diphenyl-pyrazolium methyl sulfate plus 4-Chloro-2-methylphenoxy acetic acid** | 0.50 + 0.375 | 80 | 85 | 60 | 90 | 79 |

*Rate given as pound per acre of pyrazolium cation.
**Rate given in pounds per acre of acid equivalents applied as the dimethylamine salt.

EXAMPLE 3

Wild Oat Control in the Presence of Waldron Wheat

In these tests, Waldron wheat is seeded in early May. Five days later, and several days prior to wheat emergence, wild oats (Avena spp.) emerge. When the wild oats develop to the four-leaf stage, selected plots are sprayed with aqueous solutions containing 1,2-dimethyl-3,5-diphenylpyrazolium methyl sulfate or said compound plus 2,4-dichlorophenoxy acetic acid (2,4-D).

Applications are made in such a manner as to provide 8 or 16 ounces per acre of the active pyrazolium compound alone and in combination with 6 ounces per acre of 2,4-dichlorophenoxy acetic acid (2,4-D).

Each solution also contains 0.5% by weight of the surfactant, "Surfel 4884," the linear alkyl polyoxyethylene ether marketed by Union Carbide Corporation. Eight weeks after treatment the plots are rated for wild oat and wild mustard control. Data obtained are reported below in Table III.

TABLE III

Wild Oat and Wild Mustard Control in the Presence of Waldron Wheat

| Treatment | Ounce Per Acre | % Inhibition (0–100) | | |
|---|---|---|---|---|
| | | Wild Oats | Wild Mustard | Waldron Wheat |
| 1,2-Dimethyl-3,5-diphenyl-pyrazolium methyl sulfate | 8 | 61 | 0 | 1 |
| | 16 | 78 | 10 | 3 |
| 1,2-Dimethyl-3,5-diphenyl-pyrazolium methyl sulfate | 8 + 6 (2,4-D)** | 87 | 100 | 3 |
| 1,2-Dimethyl-3,5-diphenyl-pyrazolium methyl sulfate | 16 + 6 (2,4-D)** | 87 | 100 | 3 |
| Untreated Controls | | 0 | 0 | 0 |

*Rate given as pound per acre of pyrazolium cation.
**Rate given in pounds per acre of acid equivalents applied as the dimethylamine salt.

Results comparable to those in Tables I, II, and III are obtained when other synergistic combinations of the invention are used.

EXAMPLE 4

Preparation of 1,2-Dimethyl-3,5-diphenylpyrazolium 2,4-dichlorophenoxyacetate 1,2-Dimethyl-3,5-diphenylpyrazolium methyl sulfate was converted by ion exchange chromatography to the pyrazolium hydroxide. This was then titrated ($H_2O$ solution) with 2,4-dichlorophenoxyacetic acid. Solid 2,4-D was added and went into solution after a very short time. The pH of the solution was monitored using a pH meter. Addition of the acid was stopped at pH 7 (initially pH was 12 to 13). This $H_2O$ solution was kept at room temperature for 48 hours. The pH was then approximately 8. An additional amount of acid was added until pH 7 was again obtained. After 24 hours, pH held at 7.

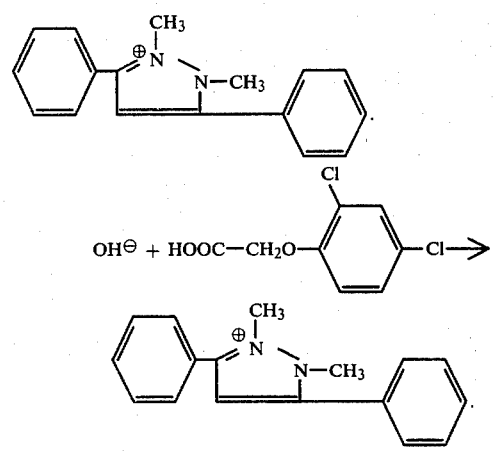

-continued

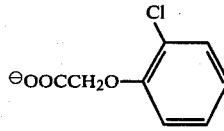

The H₂O solution was evaporated to a yellow oil and then azeotroped with toluene/acetone several times. Hexane was added with 5% to 10% dry acetone. The oil solidified to a white solid, was filtered, washed with hexane/acetone and dried. 7.0 Grams, melting point 152° C. to 154° C., of a lemon yellow solid was obtained.

Analysis Calculated for $N_2O_3Cl_2C_{25}H_{22}$: C, 63.97; H, 4.72; N, 5.96. Found: C, 63.67; H, 4.69; N, 5.90. The compound is useful as a herbicide.

EXAMPLE 5

Preparation of 1,2-Dimethyl-3,5-diphenylpyrazolium 4-chloro-2-methylphenoxyacetate 1,2-Dimethyl-3,5-diphenylpyrazolium hydroxide in a H₂O solution was titrated with 4-chloro-2-methylphenoxyacetic acid (MCPA), a known herbicide until pH 7 was obtained and retained for 48 hours. MCPA was added as a solid and slowly dissolved.

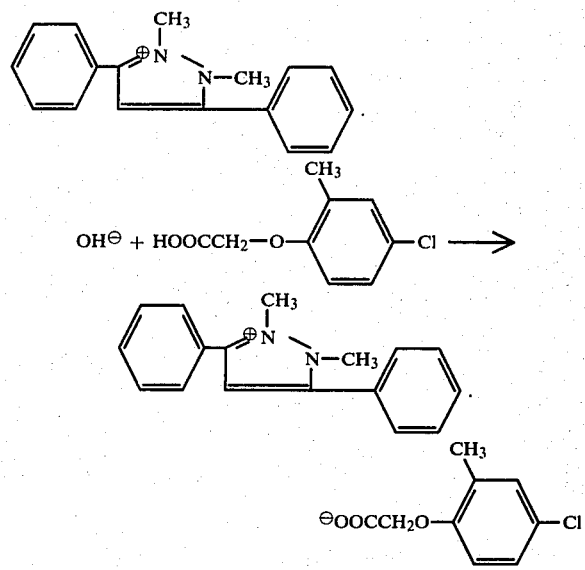

The H₂O solution was evaporated to a low volume (oil) and toluene/acetone azeotroped several times. Hexane (5% acetone) was added and the oil solidified to a light yellow solid and was filtered, washed with hexane and dried. 6.5 Grams, melting point 138° C. to 140° C. of a light yellow solid was obtained.

Analysis Calculated for $N_2O_3ClC_{26}H_{25}$: C, 69.55; H, 5.61; N, 6.24. Found: C, 68.47; H, 5.86; N, 6.42. The compound is useful as a herbicide.

The remaining examples illustrate the preparation of various pyrazolium salts (I) useful in the synergistic combinations of the invention. The pyrazolium salts (I) are conveniently prepared by first condensing the appropriate diketone with hydrazine or a C₁-C₄ lower alkyl hydrazine to form the corresponding 3,5-diphenylpyrazole. Thereafter, said pyrazole is alkylated to form the desired formula (I) pyrazolium salt.

Where hydrazine is employed in the condensation, alkylations are effected at the 1 and 2 positions. Where a lower alkyl hydrazine is employed in the initial condensation, alkylation is effected at the 2 position.

Since the diketone and hydrazine compounds combine in equimolar quantities, it is preferable to maintain the molar ratio of reactants at about 1:1; however, a slight excess (up to about 10%) of either reactant may be used.

The ring-forming reaction between the hydrazine or alkyl hydrazine and the diketone is preferably carried out by combining the reactants in a solvent and heating to the reaction temperature. Suitable temperatures are in the range of from about 70° C. to about 150° C. and, preferably, between 80° C. and 120° C. Suitable solvents include, for example, aprotic solvents, such as, xylene, toluene, benzene, pyridine, DMSO, DMF, and the like, or protic solvents, such as, C₁-C₄ alcohols preferably, n- and iso-propanol. Where the latter solvents are employed, high rates of conversion are obtained at temperatures in the range of 80° C. to 85° C.

Where hydrazine is employed in the initial condensation reaction, alkylation of the resulting pyrazole is accomplished with conventional alkylating agents, preferably in the presence of an acid acceptor, such as, an alkali metal hydroxide or alkoxide. Suitable bases include, for example, sodium methoxide, sodium hydroxide, and the like.

The alkylation reactions are preferably conducted in the presence of a solvent, such as toluene, methylisobutylketone, n- or iso-propanol or an aqueous alcohol solution, such as a mixture of n-propanol and water.

Suitable alkylation reagents include, for example, alkyl halides, alkyl acetates, alkyl sulfates, alkyl nitrates, alkyl phosphate, alkyl carbonates, alkyl hydrogen sulfates, alkyl methyl sulfates and alkyl toluene sulfonates; wherein, said alkyl groups are in the range of from C₁-C₄ to provide the appropriate alkyl substituent in the formula(I) compound.

The pyrazole and alkylating reagent combine on an equimolar basis. However, it is often preferred to employ an excess of the alkylating agent. Optimum reaction conditions for effecting the alkylations will vary depending on the reactants employed. Reaction is effected by combining the alkylating agent, the pyrazole and, preferably, the acid acceptor and solvent. Reaction often occurs at room temperature. If not, the reaction mixture is heated until the reaction occurs. Where the alkylating reagents employed are volatile, such as, methyl chloride, the reaction is preferably conducted in a sealed vessel under pressure, to avoid loss of the reactants.

Quaternization of the 1-alkylpyrazole is effected by reaction thereof with at least an equimolar quantity of an alkylating agent, such as those mentioned above.

This reaction is preferably conducted in the presence of a solvent, such as, a lower alcohol C₁-C₄; a ketone, such as, acetone, methyl isobutyl ketone, methyl ethyl ketone or cyclohexanone; a chlorinated hydrocarbon, such as, chloroform; an ether, such as, diethyl ether, methyl ethyl ether or di-n-propyl ether; a molar aprotic solvent, such as, dimethyl sulfoxide or dimethylformamide; or, preferably, an aprotic solvent, such as, xylene, toluene or benzene.

The quaternization is effected by mixing the reactants and solvent at temperatures maintained between 35° C. and 150° C., preferably between 50° C. and 125° C.

Since the 1-alkylpyrazole and alkylating reagent combine in equimolar quantities, it is preferred to employ a 1:1 molar ratio thereof; however, an excess of either reagent may be employed.

As in the previously discussed alkylation reaction, where the alkylating agent is volatile at the temperatures used, such as in the case of methyl chloride, it is preferred to use a sealed pressure vessel to conduct the reaction.

Where the diketone selected is asymetrically substituted and $R_1$ differs from $R_2$ in the formula (I) compound to be produced, a mixture of isomers will result from the above synthetic scheme. In such cases, it is generally expedient to employ the isomer mixture in the herbicidal processes of the present invention. Where their separation is desired, however, it may be effected by conventional separation techniques, such as, for example, by fractional crystallization.

In carrying out the above ring closure and alkylation reactions, it may be expedient to initially form a salt having an anion other than that which it is desired to employ in the herbicidal processes of the present invention.

The exchange may be effected by treating the initially formed salt with an ion exchange resin. Among the suitable ion exchange resins, one may mention a strong base organic anion exchanger. Illustrative exchangers employ quaternary ammonium salts. Where the resin is supplied as the salt of an anion other than that desired, it is pretreated with an aqueous solution of a salt of the desired anion. For example, if the resin is supplied as a quaternary ammonium chloride and it is desired to produce a pyrazolium nitrate, one would pretreat the resin with an aqueous solution of sodium nitrate.

Other optional subsequent modifications of the anion in the pyrazolium salt may be effected. For example, a pyrazolium chloride may be conveniently converted to the corresponding bromide or iodide by treatment with NaBr or NaI, respectively, in a solvent, such as acetone. A pyrazolium salt, such as the chloride, may be converted to the corresponding perchlorate by treatment of an aqueous solution of said salt with perchloric acid. However, the pyrazolium perchlorates differ measurably from other pyrazolium salts in that they exhibit extremely poor water solubility and are substantially more difficult to formulate since there is about a 100- to 1000-fold difference in their solubilities as compared with the other salts. This results in the precipitation of the less soluble perchlorate salt. The bromides or iodides may be conveniently converted to the tribromides or triiodides by adding bromine or iodine to a solution of the mono-bromide or mono-iodide in a solvent, such as ethanol.

EXAMPLE 6

Preparation of 1-Methyl-3,5-diphenylpyrazole

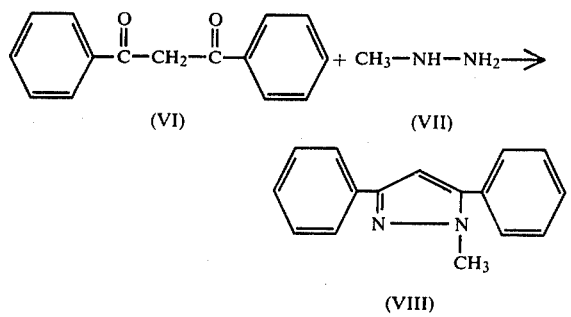

545.0 Grams (2.43 moles) of dibenzoylmethane and 533 ml. of pyridine are stirred together and heated to 80° C. 112 Grams (2.43 moles) of methylhydrazine are then slowly added to the mixture and a strong exothermic reaction ensues necessitating cooling of the mixture with a water bath. When addition is complete, the mixture is heated to reflux and maintained in this condition for 40 minutes. The mixture is then cooled to 30° C., poured into 19 liters of 3 N HCl, filtered, and the solid collected. This is reslurried in 198 grams (2.43 moles) of sodium acetate dissolved in 19 liters of water. The mixture is filtered, water washed and air dried to give 535 grams of product, 94.5% yield, having melting point 58° C. to 59° C.

Following the above procedure and substituting ethylhydrazine, n-propylhydrazine, isopropylhydrazine, sec-butylhydrazine, n-butylhydrazine, or isobutylhydrazine for methylhydrazine in the above reaction yields respectively: 1-ethyl-3,5-diphenylpyrazole; 1-n-propyl-3,5-diphenylpyrazole; 1-isopropyl-3,5-diphenylpyrazole; 1-sec-butyl-3,5-diphenylpyrazole; 1-n-butyl-3,5-diphenylpyrazole; and 1-isobutyl-3,5-diphenylpyrazole.

EXAMPLE 7

Reaction of the appropriately substituted dibenzoylmethane with the appropriate alkylhydrazine under the conditions of Example 6 results in the preparation of 1-alkyl-3,5-substituted diphenylpyrazoles. Graphically, the process may be illustrated as follows:

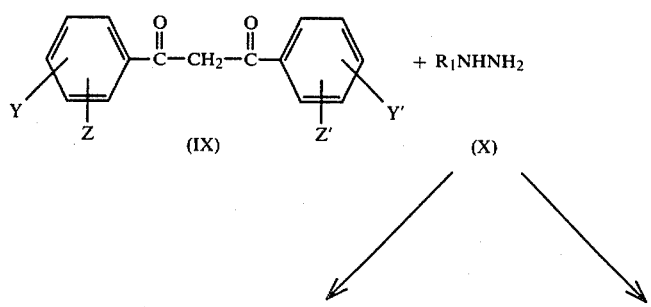

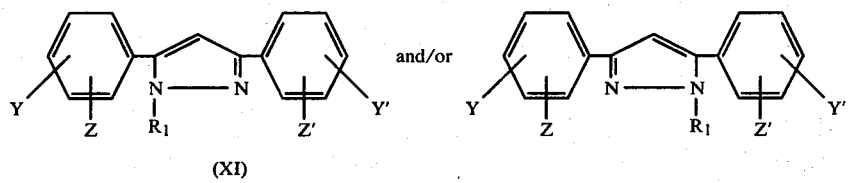

Among the compounds which can be prepared by this reaction are those identified in the Table below. For compounds in this Table, Y' and Z' are both hydrogen.

TABLE IV

| Y | Z | $R_1$ | m.p. °C. |
|---|---|---|---|
| Cl (3) | H | $CH_3$ | |
| Cl (4) | H | $CH_3$ | 127.5–128.5 |
| Br (4) | H | $CH_3$ | |
| $CH_3$ (4) | H | $CH_3$ | 101.5–103 |
| $OCH_3$ (3) | H | $CH_3$ | |
| $OCH_3$ (4) | H | $CH_3$ | 105–106.5 |
| Cl (3) | Cl (4) | $CH_3$ | |
| Br (3) | Br (5) | $C_2H_5$ | |
| Br (3) | Cl (4) | $CH_3$ | |
| $CH_3$ (2) | $CH_3$ (6) | $CH_3$ | |
| $OCH_3$ (3) | $OCH_3$ (4) | $C_3H_7$-n | |
| Cl (4) | H | $C_4H_9$-sec | |
| Br (3) | H | $C_4H_9$-n | |
| $CH_3$ (4) | Cl (3) | $CH_3$ | |
| $CH_3$ (3) | $OCH_3$(4) | $CH_3$ | |
| $OCH_3$ (4) | H | $C_4H_9$-sec | |

EXAMPLE 8

Preparation of 1,2-Dimethyl-3,5-diphenylpyrazolium p-toluene sulfonate

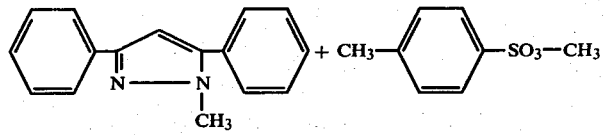

400 Grams (1.71 moles) of 1-methyl-3,5-diphenylpyrazole is dissolved in 2100 ml. of xylene and the solution thus prepared dried by azeotropic distillation. The solution is cooled to 70° C. and 318 grams (1.71 moles) of methyl-p-toluene sulfonate is added. The mixture is then refluxed for one hour and cooled causing the product to crystallize. When the mixture is cooled to 40° C., 1000 ml. of acetone are added. The mixture is filtered, washed with acetone, and dried in vacuo yielding 495 grams (69%) of product having a melting point of 177° C. to 178° C.

EXAMPLE 9

Preparation of 1,2-Dimethyl-3,5-diphenylpyrazolium iodide 5.0 Grams of 1-methyl-3,5-diphenylpyrazole is dissolved in 30 ml. of dry benzene with heating and constant stirring. 30.4 Grams of methyl iodide is added to the mixture, and the mixture heated to reflux. After refluxing for 12 hours, the mixture is cooled and filtered. The filtrate is again refluxed and as product forms, it is separated from the mixture by filtration. The total amount of solid recovered is 1.21 grams, 15% yield, having a melting point of 167° C. to 169° C.

EXAMPLE 10

Preparation of 1,2-Dimethyl-3,5-diphenylpyrazolium hydrogen sulfate and methyl sulfate 5.0 Grams of 1-methyl-3,5-diphenylpyrazole is dissolved in 30 ml. of dry xylene with heating and constant stirring. The solution is cooled to 60° C., and 2.78 grams of dimethyl sulfate is added in 10 ml. of xylene. The mixture is then heated to 100° C. for 6 hours and allowed to cool. After cooling, the mixture is filtered. The solid which is recovered is stirred with dry acetone and the mixture filtered. This yields 3.91 grams of the methyl sulfate, 50.7% yield, having a melting point of 146° C. to 148° C.

The filtrate is then evaporated to remove acetone and the remaining residue is collected. The residue weight of 1.23 grams, 16.6% yield, is the desired hydrogen sulfate having a melting point of 188° C. to 189.5° C.

EXAMPLE 11

Following the general procedures of Examples 8, 9 or 10 substituting the appropriately substituted 1-alkyl-3,5-substituted diphenylpyrazole for 1-methyl-3,5- diphenylpyrazole and the appropriate alkyl-p-toluene sulfonate, alkyl halide or alkyl sulfate for the methyl-p-toluene sulfonate, methyl iodide or dimethyl sulfate, yields the corresponding 1,2-dialkyl substituted 3,5-diphenylpyrazolium salt. The reaction is graphically illustrated below:

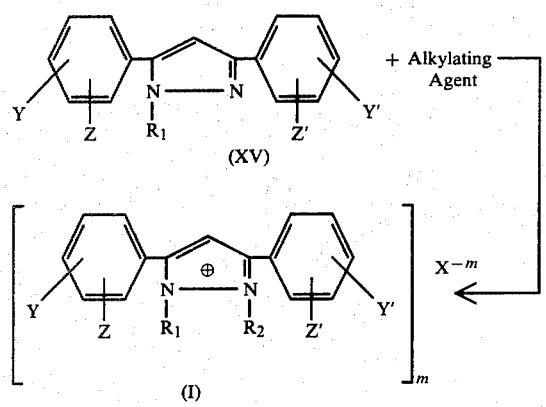

wherein $R_1$, $R_2$, X, Y, Y', Z, Z' and m are as described above for (I). Among the compounds which can be prepared by this reaction are those identified in the table below, where Y' and Z' are both hydrogen a rate sufficient to maintain reflux. Thirty minutes after addition, the reaction is complete. The reaction mixture is permitted to cool and is then poured into water. The desired product as a fine white solid precipitates and is filtered, washed with cold water and dried, yielding 22.1 grams of product, melting point 198.5° C. to 200.5° C.

EXAMPLE 13

Preparation of 1-Methyl-3,5-diphenylpyrazole 5.0 Grams of dibenzoylmethane in 40 ml. of isopropanol is heated to 50° C. The temperature of the reaction mixture is then raised to about 85° C. and 10.5 grams of methyl hydrazine in 10 ml. of isopropanol added thereto. The mixture is heated at this temperature for 30 minutes, then cooled and cold water added thereto. A white solid precipitate forms and is filtered, washed and dried to yield 5.22 grams of product having a melting point of 59.5° C. to 60° C., 99+% yield.

EXAMPLE 14

Preparation of 1,2-Dimethyl-3,5-diphenylpyrazolium perchlorate 4.7 Grams (0.02 moles) of 1-methyl-3,5-diphenylpyrazole is added to a solution of methyl chloride, 1.5 grams (0.03 moles) in 35 ml. of n-propanol maintained at −40° C. The mixture is then heated to 100° C. and

TABLE V

| | | | Reactants and Products | | | |
|---|---|---|---|---|---|---|
| Y | Z | $R_1$ | Alkylating Agent | $R_2$ | 122 | melting point °C. |
| Cl (3) | H | $CH_3$ | $CH_3$—⌬—$SO_2$—$OCH_3$ | $CH_3$ | $C_7H_7SO_3$ | |
| Br (4) | H | $CH_3$ | $CH_3$—⌬—$SO_2$—$OC_2H_5$ | $C_2H_5$ | $C_7H_7SO_3$ | |
| $CH_3$ (4) | H | $CH_3$ | $(CH_3)_2SO_4$ | $CH_3$ | $CH_3SO_4$ | 174–176 |
| $OCH_3$ (3) | H | $CH_3$ | $CH_3$—⌬—$SO_2$—$OCH_3$ | $CH_3$ | $C_7H_7SO_3$ | |
| Cl (3) | 2(4) | $CH_3$ | $CH_3I$ | $CH_3$ | I | |
| Br (3) | Br (5) | $C_2H_5$ | $C_2H_5I$ | $C_2H_5$ | I | |
| $CH_3$ (2) | $CH_3$ (6) | $CH_3$ | $n$-$C_3H_7I$ | $C_3H_7$-n | I | |
| $F_3$ | H | $CH_3$ | $(CH_3)_2SO_4$ | $CH_3$ | $CH_3SO_4$ | 120–112 |
| $OCH_3$ (3) | $OCH_3$ (4) | $C_3H_7$-n | $i$-$C_3H_7Br$ | $C_3H_7$-i | Br | |
| Cl (4) | H | $C_4H_9$-sec | $CH_3I$ | $CH_3$ | I | |
| Cl (4) | H | $C_4H_9$-sec | sec-$C_4H_9Br$ | $C_4H_9$-sec | Br | |
| $CH_3$ (4) | Cl (3) | $CH_3$ | $CH_3I$ | $CH_3$ | I | |
| $OCH_3$ (4) | H | $CH_3$ | $(CH_3)_2SO_4$ | $CH_3$ | $CH_3SO_4$ | 137–138.5 |
| $OCH_3$ (4) | H | $CH_3$ | $CH_3$—⌬—$SO_3CH_3$ | $CH_3$ | $C_7H_7SO_3$ | 127.5–129 |
| H | H | $CH_3$ | $(C_3H_5)_2SO_4$ | $C_2H_5$ | $C_2H_5SO_4$ | 109–111 |
| $CH_3$ (4) | H | $CH_3$ | $CH_3$—⌬—$SO_2OCH_3$ | $CH_3$ | $C_7H_7SO_2$ | 150–151.5 |

EXAMPLE 12

Preparation of 3,5-Diphenylpyrazole 22.4 Grams (0.10 moles) of dibenzoylmethane in 200 ml. of isopropyl alcohol are heated to reflux (approximately 85° C.), and to this is added hydrazine hydrate at evaporated to a bright green oil. On addition of hexane and cooling, the pyrazolium chloride as a green solid precipitates. The solid is washed with water and dissolved in 60 ml. of $H_2O$ and then $HClO_4$ added. The pyrazolium perchlorate as a white precipitate forms. It is filtered, washed with water and dried to yield the desired product.

EXAMPLE 15

Preparation of 1,2-Dimethyl-3,5-diphenylpyrazolium Methylsulfate

375 Grams (1.6 moles) of 1-methyl-3,5-diphenylpyrazole is dissolved in 1850 ml. of dry xylene and heated to 60° C. 208.13 Grams (1.65 moles) of dimethylsulfate in 150 ml. of dry xylene is then added and the temperature of the reaction mixture raised to 105° C. to 110° C. and maintained there for 7.5 hours. The mixture is allowed to cool and then filtered. A brown solid is recovered, washed with xylene and then dry acetone to give the product in 88% yield, having a melting point of 155° C. to 157° C.

EXAMPLE 16

Preparation of 1,2-Dimethyl-3,5-diphenylpyrazolium bromide

A glass column is packed with a commercial grade of a trimethyl benzyl ammonium chloride, strong base organic anion exchange resin. The resin is washed thoroughly with an aqueous sodium bromide solution of 1 N concentration until $Br^-$ ion is detected in the eluent. Then an aqueous solution of 1,2-dimethyl-3,5-diphenylpyrazolium p-toluene sulfonate is passed down the column at a slow rate. The eluent is concentrated in vacuo, leaving the desired product as a residue after drying with a melting point of 188° C.-189° C.

Analysis: Calcd. for $C_{17}H_{17}N_2Br$: C, 62.01; H, 5.22; N, 8.54; Br, 24.22. Found: C, 61.98; H, 5.30; N, 8.54; Br, 24.27.

EXAMPLE 17

Following the general procedure of Example 16 above, substituting the appropriate sodium salt for the sodium bromide used therein and the appropriate pyrazolium p-toluene sulfonate for that used therein yields the compounds having the following formula and substituents set forth in the table below.

TABLE III

| Melting Point °C. | $R_1$ | $R_2$ | X |
|---|---|---|---|
| 100.5–103 | $CH_3$ | $CH_3$ | $OH . (3H_2O)$ |
| 56–58 | $CH_3$ | $CH_3$ | $½ SO_4 . (2H_2O)$ |
| 140–141.5 | $CH_3$ | $CH_3$ | $NO_3$ |
| 188–189 | $CH_3$ | $CH_3$ | Br |
| 179.5–181 | $CH_3$ | $CH_3$ | $Cl . ½ H_2O$ |
| 168–169 | $CH_3$ | $CH_3$ | I |

EXAMPLE 18

Preparation of 1,2-Dimethyl-3,5-diphenylpyrazolium perchlorate

To a solution of 1,2-dimethyl-3,5-diphenylpyrazolium p-toluene sulfonate (10.0 g.) in 500 ml. of water is added a 20% aqueous solution of perchloric acid with vigorous stirring. The product separates immediately as a white solid. It is collected by filtration, washed with water and dried to give 8.3 g. of the desired product having a melting point of 183° C.–184° C., and the following elemental analysis: Calcd. for $C_{17}H_{17}ClN_2O_4$: C, 58.75; H, 4.92; N, 8.05. Found: C, 58.21; H, 4.84; N, 7.95.

EXAMPLE 19

Following the general procedure of Example 18, substituting the appropriate pyrazolium p-toluene sulfonate for that used therein results in the formation of the perchlorates set forth in the table below.

TABLE VI

| Substituents | | | | |
|---|---|---|---|---|
| Y | Z | $R_1$ | $R_2$ | m.p. °C. |
| H | H | $CH_3$ | $-C_3H_7$-n | 145–146.5 |

EXAMPLE 20

Preparation of 1,2-Dimethyl-3,5-diphenylpyrazolium triiodide

To a solution of 2.0 grams (0.0053 moles) of 1,2-dimethyl-3,5-diphenylpyrazolium iodide in 100 ml. of aqueous ethanol (1:1) was added 1.34 grams (0.0053 moles) of iodine. The reaction mixture was allowed to sit with the resultant formation of a red precipitate.

The precipitate was collected by filtration, washed with aqueous ethanol and air dried to produce 3.0 grams of the desired triiodide having a melting point of 108°–110° C. and the following elemental analysis:

Calculated: C, 32.41% H, 2.72%; N, 4.44%; I, 61.45% Found: C, 32.23%; H, 2.78%; N, 4.43%; I, 60.29%.

EXAMPLE 21

Following the general ring closing procedure of Example 4 and the alkylation procedure of Example 9, employing methylhdydrazine and the appropriate diketones and alkylating agents yields the pyrazolium salts of the following formula, having the substituents set forth in the table below.

TABLE VII $$\left[ \text{Ar-C(Y,Z)=N(R_1)-N(R_2)=C(Y',Z')-Ar} \right]_m \cdot X^{-m}$$

(Structure: two aryl rings with substituents Y, Y', Z, Z' connected through a pyrazolium-like cation N⊕—N with substituents $R_1$ and $R_2$; counterion $X^{-m}$)

| X | Y | Y' | Z | Z' | $R_1$ | $R_2$ | Melting Point °C. |
|---|---|---|---|---|---|---|---|
| $-OSO_2-C_6H_4-CH_3$ | H | Cl (4) | H | H | $CH_3$ | $CH_3$ | 177.5–179 |
| $-O-SO_3-CH_3$ | H | Cl (4) | H | H | $CH_3$ | $CH_3$ | over 340 |
| $-O-SO_3-CH_3$ | H | Cl (4) | H | H | $CH_3$ | $CH_3$ | 217–219 |
| $ClO_4$ | H | Cl (4) | H | H | $CH_3$ | $CH_3$ | 136.5–138 |
| $ClO_4$ | H | H | H | H | $CH_3$ | $C_3H_7$-n | 145–146.5 |
| $C_2H_5O-SO_2-O$ | H | H | H | H | $CH_3$ | $C_2H_5$ | 109–111 |
| $CH_3O-SO_2-O$ | H | Cl (4) | H | H | $CH_3$ | $CH_3$ | 136.5–138 |
| $CH_3O-SO_2-O$ | H | $CH_3$ (4) | H | H | $CH_3$ | $CH_3$ | 107–110 |
| $ClO_4$ | H | Cl (3) | H | H | $CH_3$ | $CH_3$ | 157–160 |
| $ClO_4$ | H | Cl (2) | H | H | $CH_3$ | $CH_3$ | 124–128 |
| $CH_3O-SO_2-O$ | H | $CH_3$ (3) | H | H | $CH_3$ | $CH_3$ | 97–100 |
| $ClO_4$ | H | $CH_3$ (2) | H | H | $CH_3$ | $CH_3$ | 166–170 |
| $ClO_4$ | H | $CH_3O$ (4) | H | H | $CH_3$ | $CH_3$ | 152–156 |
| $CH_3O-SO_2-O$ | H | Cl (3) | H | Cl (5) | $CH_3$ | $CH_3$ | 162–164 |
| $HSO_4$ | H | Cl (2) | H | H | $CH_3$ | $CH_3$ | purple gum |
| $CH_3O-SO_2-O$ | H | $CH_3$ (2) | H | H | $CH_3$ | $CH_3$ | brown gum |
| $ClO_4$ | Cl (3) | H | Cl (5) | H | $CH_3$ | $CH_3$ | 183–185 |
| $CH_3O-SO_2-O$ | Cl (3) | H | Cl (4) | H | $CH_3$ | $CH_3$ | 152–153 |

EXAMPLE 22

Wild Oat and Broadleaf Control in the Presence of Winter Wheat

Test plots are seeded with winter wheat (Var. McCall). When the wheat is in the 3 to 6 leaf stage and the heavy wild oat infestation is in the 2 to 3 leaf stage, the plots are treated with an aqueous spray containing 1,2-dimethyl-3,5-diphenylpyrazolium methyl sulfate, or said compound in combination with the dimethylamine salt of 2,4-dichlorophenoxy acetic acid. The spray is applied under a pressure of 2.81 kg/cm$^2$ and at the rate of 93.54 l/ha. Each of the above treatments is replicated three times, and the 1.83 × 9.14 m size plots are arranged in a randomized complete block design.

After treatment there is an initial injury of 5 to 7% to the wheat, from which the plants recover. One month after the treatment the percent control of wild oats and broadleaf weeds achieved is determined. The thus obtained data are averaged and summarized in Table VIII below.

EXAMPLE 23

Wild Oat Control in the Presence of Barley

Test plots are seeded with barley (var. C.M. 76). When the barley is mostly in the 3 leaf stage and about seventy percent of the moderate infestation of wild oats is in the 3 leaf stage, the plots are treated with an aqueous spray containing 1,2-dimethyl-3,5-diphenylpyrazolium methyl sulfate, or said compound in combination with the mixed ethanolamine and isopropanolamine salts of 2,4-dichlorophenoxy acetic acid. The spray is applied under a pressure of 1.76 kg/cm$^2$ and at the rate of 299.3 l/ha. Each of the above treatments is replicated three times, and the 6.1 × 30.5 m size plots are arranged in a randomized complete block design.

Three months after treatment the percent control of wild oats achieved (and barley injury: 1–1.7%) is determined, and at harvest, the yield per plot is measured. The thus obtained data are averaged and summarized in Table IX below.

Table VIII

Efficacy of 1,2-Dimethyl-3,5-diphenylpyrazolium Methyl Sulfate Alone and in Combination with the Dimethylamine Salt of 2,4-Dichlorophenoxy Acetic Acid for the Control of Wild Oats and Broadleaf Weeds in the Presence of Winter Wheat

| Compound | Active Ingredient kg/ha | Percent Control (Average of 3 Replicates) | | | |
|---|---|---|---|---|---|
| | | Pepperweed | Pennycress | Shepherdspurse | Wild Oats |
| 1,2-Dimethyl-3,5-diphenyl-pyrazolium methyl sulfate | 1.12 | 1.0 | 1.0 | 1.0 | 98.0 |
| 1,2-Dimethyl-3,5-diphenyl-pyrazolium methyl sulfate + Dimethylamine Salt of 2,4-dichlorophenoxy acetic acid | 1.12 + 0.56 | 97.7 | 97.7 | 97.7 | 98.0 |

Table IX

Efficacy of 1,2-Dimethyl-3,5-diphenylpyrazolium Methyl Sulfate Alone and in Combination with Mixed Amine Salts of 2,4-Dichlorophenoxy Acetic Acid for the Control of Wild Oats in the Presence of Barley

| Compound | Active Ingredient kg/ha | Percent Control (Average of 3 Replicates) of Wild Oats | Yield: kg/plot |
|---|---|---|---|
| 1,2-Dimethyl-3,5-diphenyl-pyrazolium methyl sulfate | 0.84 | 71.7 | 49.58 |
| 1,2-Dimethyl-3,5-diphenyl-pyrazolium methyl sulfate<br>+<br>Mixed amine salts of 2,4-dichlorophenoxy acetic acid | 0.84<br><br>+<br>0.56 | 88.3 | 54.75 |
| Control | — | 1.0 | 44.45 |

EXAMPLE 24

Wild Oat and Broadleaf Weed Control in the Presence of Barley

Test plots are seeded with barley (var. Luther). When the barley is in the 5 to 6 leaf stage and the heavy infestation of wild oats is in the 4 to 5 leaf stage, the plots are treated with an aqueous spray containing 1,2-dimethyl-3,5-diphenylpyrazolium methyl sulfate, or said compound in combination with the dimethylamine salt of 2,4-dichlorophenoxy acetic acid. The spray is applied under a pressure of 2.81 kg/cm² and at the rate of 93.54 l/ha. Each of the above treatments is replicated three times, and the 1.83×9.14 m size plots are arranged in a randomized complete block design.

After treatment there is an initial injury of 6% to the barley from which the plants recover. One month after treatment the percent control of wild oat and broadleaf weeds achieved is determined. The thus obtained data are averaged and summarized in Table X below.

Table X

Efficacy of 1,2-Dimethyl-3,5-diphenylpyrazolium Methyl Sulfate Alone and in Combination with the Dimethylamine Salt of 2,4-Dichlorophenoxy Acetic Acid for the Control of Wild Oats and Broadleaf Weeds in the Presence of Barley

| Compound | Active Ingredient kg/ha | Percent Control (Average of 3 Replicates) | | | |
|---|---|---|---|---|---|
| | | Dandelion | Pennycress | Shepherdspurse | Wild Oats |
| 1,2-Dimethyl-3,5-diphenyl-pyrazolium methyl sulfate | 1.12 | 1.0 | 1.0 | 1.0 | 97.3 |
| 1,2-Dimethyl-3,5-diphenyl-pyrazolium methyl sulfate<br>+<br>Dimethylamine salt of 2,4-dichlorophenoxy acetic acid | 1.12<br><br>+<br>0.56 | 97.7 | 97.7 | 97.7 | 98.0 |

EXAMPLE 25

Wild Oat and Broadleaf Weed Control in the Presence of Barley

Test plots are seeded with barley (var. Steveland). When the barley is in the 4 leaf stage and the moderately heavy infestation of wild oats is in the 3 to 4 leaf stage, the plots are treated with an aqueous spray containing 1,2-dimethyl-3,5-diphenylpyrazolium methyl sulfate, or said compound in combination with the dimethylamine salt of 2,4-dichlorophenoxy acetic acid; or said compound in combination with the isooctyl ester of 2,4-dichlorophenoxy acetic acid. The spray is applied under a pressure of 2.81 kg/cm² at the rate of 93.54 l/ha. Each of the above treatments is replicated three times, and the 1.83×9.14 m size plots are arranged in a randomized complete block design.

One month after treatment the percent control of wild oats and broadleaf weeds achieved is determined. The thus obtained data are averaged and summarized in Table XI below.

Table XI

Efficacy of 1,2-Dimethyl-3,5-diphenylpyrazolium Methyl Sulfate Alone or in Combination with the Dimethylethylamine Salt of-, or the Isooctyl Ester of 2,4-Dichlorophenoxy Acetic Acid for the Control of Wild Oats and Broadleaf Weeds in the Presence of Barley

| Compounds | Active Ingredient kg/ha | Percent Control Average of 3 Replicates) | | |
|---|---|---|---|---|
| | | Pennycress | Pigweed | Wild Oats |
| 1,2-Dimethyl-3,5-diphenyl-pyrazolium methyl sulfate | 1.12 | 1.0 | 1.0 | 91.3 |
| 1,2-Dimethyl-3,5-diphenyl-pyrazolium methyl sulfate<br>+<br>Dimethylamine salt of 2,4-dichlorophenoxy acetic acid | 1.12<br><br>+<br>0.28 | 96.0 | 96.0 | 92.0 |
| 1,2-Dimethyl-3,5-diphenyl-pyrazolium methyl sulfate<br>+<br>Dimethylamine salt of 2,4-dichlorophenoxy acetic acid | 1.12<br><br>+<br>0.56 | 97.7 | 97.7 | 91.3 |
| 1,2-Dimethyl-3,5-diphenyl-pyrazolium methyl sulfate<br>+<br>Isooctyl ester of 2,4-dichlorophenoxy acetic acid | 1.12<br><br>+<br>0.14 | 97.3 | 97.3 | 94.0 |
| 1,2-Dimethyl-3,5-diphenyl-pyrazolium methyl sulfate<br>+<br>Isooctyl ester of 2,4-di- | 1.12<br><br>+ | 98.0 | 98.0 | 96.0 |

Table XI-continued

Efficacy of 1,2-Dimethyl-3,5-diphenylpyrazolium Methyl Sulfate Alone or in Combination with the Dimethylethylamine Salt of-, or the Isooctyl Ester of 2,4-Dichlorophenoxy Acetic Acid for the Control of Wild Oats and Broadleaf Weeds in the Presence of Barley

| Compounds | Active Ingredient kg/ha | Percent Control Average of 3 Replicates) | | |
|---|---|---|---|---|
| | | Pennycress | Pigweed | Wild Oats |
| chlorophenoxy acetic acid | 0.28 | | | |

EXAMPLE 26

Wild Oat and Broadleaf Weed Control in the Presence of Barley

Test plots are seeded with barley (var. Mora ian). When the barley is in the 4 to 5 leaf stage and the heavy infestation of wild oats is in the 3 to 5 leaf stage, the plots are treated with an aqueous spray containing 1,2-dimethyl-3,5-diphenylpyrazolium methyl sulfate, or said compound in combination with the dimethylamine salt of 2,4-dichlorophenoxy acetic acid. The spray is applied under a pressure of 2.81 kg/cm² at the rate of 74.83 l/ha. Each of the above treatment is applied to a single plot, 7.3×50.1 m in size.

Two and a half months after treatment the percent control of wild oats and broadleaf weeds, and at harvest time the yield are determined. The thus obtained data are summarized in Table XII below.

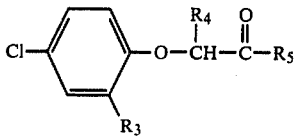

wherein $R_3$ is Cl or methyl; $R_4$ is hydrogen or methyl; $R_5$ is $-OR_6$ or $-OM$; $R_6$ is hydrogen, alkyl $C_1$-$C_8$, or alkoxyalkyl $C_2$-$C_8$; and M is an alkali metal ion,

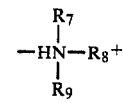

or $-NH^+(H)_n(R_{10}OH)_{n'}$; $R_7$, $R_8$ and $R_9$ are hydrogen

Table XII

Efficacy of 1,2-Dimethyl-3,5-diphenylpyrazolium Methyl Sulfate alone and in Combination with the Dimethylamine Salt of 2,4-Dichlorophenoxy Acetic Acid for the Control of Wild Oats and Broadleaf Weeds in the Presence of Barley

| Compound | Active ingredient kg/ha | Percent Control | | | Yield kg/ha |
|---|---|---|---|---|---|
| | | Kochia | Wild Buckwheat | Wild Oats | |
| 1,2-Dimethyl-3,5-diphenyl-pyrazolium methyl sulfate | 1.12 | 0 | 0 | 91 | 3611.4 |
| 1,2-Dimethyl-3,5-diphenyl-pyrazolium methyl sulfate + Dimethylamine salt of 2,4-dichlorophenoxy acetic acid | 1.12 + 0.56 | 90 | 90 | 92 | 4033.9 |
| Control | — | | | | 3590.0 |

I claim:

1. A snyergistic herbicidal combination for the simultaneous control of wild oat and broadleaf weeds comprising a herbicidally effective amount of
   (a) a 1,2-dialkyl-3,5-diphenylpyrazolium salt of the formula

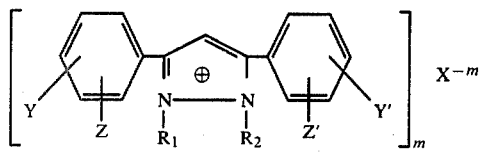

wherein $R_1$ is methyl; $R_2$ is alkyl $C_1$-$C_4$; X is a chloride, bromide, iodide, acetate, hydroxide, hydrogen sulfate, methyl sulfate, p-toluene sulfonate or perchlorate anion, Y, Y', Z, and Z' are hydrogen, halogen, methyl or methoxy; and m is 1; provided that only one phenyl ring can be substituted on the carbon para to the pyrazolium ring with a substituent other than hydrogen; and
   (b) a phenoxyacetic acid, ester or salt, of the formula:

or alkyl $C_1$-$C_4$; $R_{10}$ is alkylene $C_1$-$C_4$; n is an integer 0,1 or 2; n' is an integer 1, 2 or 3 and the sum of n and n' is 3; or mixtures of the acid, ester or salt, said amount being sufficient to provide from about 0.25 to 2.0 pounds per acre of the pyrazolium cation and from about 0.13 pound to 1.0 pound per acre of the halophenoxy compound when applied in the field.

2. A herbicidal combination according to claim 1 wherein $R_3$ is chlorine; $R_4$ is hydrogen and $R_5$ is as described in said claim 1.

3. A herbicidal combination according to claim 1, wherein $R_3$ is methyl; $R_4$ is hydrogen and $R_5$ is as described in said claim 1.

4. A herbicidal combination according to claim 1, wherein the pyrazolium salt is 1,2-dimethyl-3,5-diphenylpyrazolium methyl sulfate and the phenoxy compound is 2,4-dichlorophenoxyacetic acid or an ester or salt thereof.

5. A herbicidal combination according to claim 1 wherein the pyrazolium salt is 1,2-dimethyl-3,5-diphenylpyrazolium methyl sulfate and the phenoxy compound is 4-chloro-2-methylphenoxy acetic acid or an ester or salt thereof.

6. A herbicidal combination according to claim 1, containing a herbicidally effective amount of a pyrazolium salt of claim 1, and a mixture of a 2,4-dichlorophenoxyacetic acid or ester or salt thereof, and a 4-chloro-2-methylphenoxyacetic acid or ester or salt thereof.

7. A method for the control of wild oats and undesirable broadleaf weeds comprising, applying to the foliage of the undesirable plant species an aqueous spray of a herbicidally effective amount of a synergistic combination comprising
   (a) a 1,2-dialkyl-3,5-diphenylpyrazolium salt of the formula

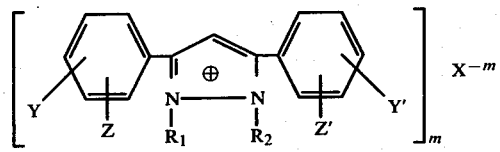

wherein $R_1$ is methyl; $R_2$ is alkyl $C_1$–$C_4$; X is a chloride, bromide, iodide, acetate, hydroxide, hydrogen sulfate, methyl sulfate, p-toluene sulfonate or perchlorate anion; Y, Y', Z and Z' are hydrogen, halogen, methyl or methoxy; and m is 1; provided that only one phenyl ring can be substituted on the carbon para to the pyrazolium ring with a substituent other than hydrogen; and
   (b) a phenoxyacetic acid, ester or salt, of the formula:

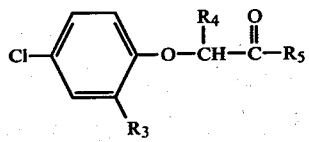

where $R_3$ is Cl or methyl; $R_4$ is hydrogen or methyl; $R_5$ is —$OR_6$ or OM; $R_6$ is hydrogen, alkyl $C_1$–$C_8$ or alkoxyalkyl $C_2$–$C_8$; and M is an alkali metal ion,

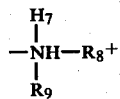

or —NH+(H)$_n$($R_{10}$OH)$_{n'}$; $R_7$, $R_8$ and $R_9$ are hydrogen or alkyl $C_1$–$C_4$; $R_{10}$ is alkylene $C_1$–$C_4$; n is an integer 0, 1 or 2; n' is an integer 1, 2 and 3 and the sum of n and n' is 3; or mixtures of the acid, ester or salt.

8. A method for the selective postemergence control of wild oats and undesirable broadleaf weeds in the presence of an agronomically important crop comprising, applying to the foliage of the undesirable plant species an aqueous mixtue containing a herbicidally effective amount of the synergistic combination according to claim 7.

9. A method according to claim 8, wherein the herbicidal combination of the pyrazolium salt and the halophenoxy compound is applied to the foliage of wild oats and undesirable broadleaf weeds in sufficient amount to provide from about 0.5 pound to 1.0 pound per acre of the pyrazolium cation and from about 0.25 pound to 0.50 pound per acre of the halophenoxy compound.

10. A method for controlling wild oats and undesirable broadleaf weeds comprising, applying to the foliage of the undesirable vegetation a herbicidally effective amount of a compound of the formula:

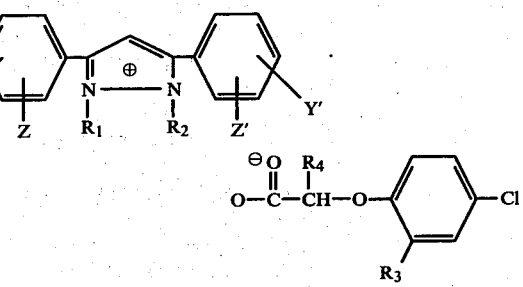

wherin $R_1$ is methyl, $R_2$ is alkyl $C_1$–$C_4$, $R_3$ is Cl or methyl, $R_4$ is hydrogen or methyl, Y, Y', Z, and Z' are hydrogen, halogen, methyl or methoxy.

11. A method for the selective postemergence control of wild oats and undesirable broadleaf weeds in the presence of an agronomically important crop comprising, applying to the foliage of the undesirable plant species an aqueous mixture containing a herbicidally effective amount of a compound of the formula:

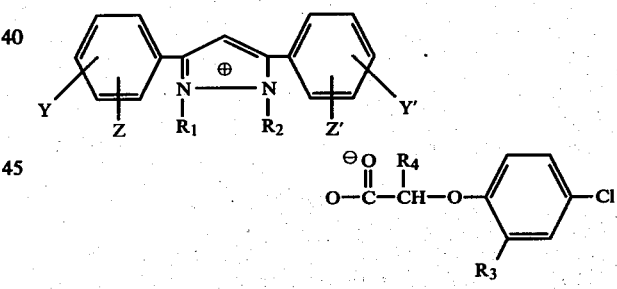

wherein $R_1$ is methyl, $R_2$ is alkyl $C_1$–$C_4$, $R_3$ is Cl or methyl, $R_4$ is hydrogen or methyl, Y, Y', Z, and Z' are hydrogen, halogen, methyl or methoxy.

* * * * *